United States Patent [19]
Mason

[11] 3,941,356
[45] Mar. 2, 1976

[54] METHOD AND APPARATUS FOR CONTINUOUS MIXING OF BLOOD PLASMA AND ADDITIVES

[75] Inventor: William H. Mason, Woodbridge, Conn.

[73] Assignee: The United States of America as represented by the Department of Health, Education and Welfare, Washington, D.C.

[22] Filed: Nov. 13, 1974

[21] Appl. No.: 523,533

[52] U.S. Cl.............. 259/7; 23/258.5 R; 62/392; 62/396; 128/400; 165/141
[51] Int. Cl.² .......................................... B01F 7/20
[58] Field of Search .............. 195/1.7, 1.8; 424/101; 259/7, 8, 23, 24, 43, 44; 23/258.5, 285; 128/400, DIG. 22; 62/389, 392, 390, 396, 394; 165/140, 141; 159/2 E

[56] References Cited
UNITED STATES PATENTS

| | | | |
|---|---|---|---|
| 2,375,558 | 5/1945 | Hutchinson | 259/23 |
| 2,396,235 | 3/1946 | Arvins | 165/141 |
| 2,541,069 | 2/1951 | Jones | 165/140 |
| 2,845,929 | 8/1958 | Strumia | 128/400 |
| 2,876,769 | 3/1959 | Cordova | 128/400 |
| 3,256,883 | 6/1966 | Wall | 128/400 |
| 3,280,899 | 10/1966 | Brasie | 165/109 |
| 3,332,468 | 7/1967 | Dietze | 159/2 E |
| 3,620,684 | 11/1971 | Brooks | 23/285 |
| 3,731,731 | 5/1973 | Bach et al. | 165/154 |
| 3,764,271 | 10/1973 | Brumfield | 128/400 |
| 3,807,958 | 4/1974 | Brumfield | 128/400 |

*Primary Examiner*—Robert W. Jenkins
*Attorney, Agent, or Firm*—Browdy and Neimark

[57] ABSTRACT

A method and apparatus for continuous mixing of blood plasma with additives, such as alcohol, comprises an elongated cylindrical chamber with inner and outer coolant chambers disposed adjacent thereto with an intermediate product chamber containing an impeller. Plasma and at least one additive are introduced into the product chamber in the vicinity of the impeller which mixes the blood plasma and additives. The blood plasma and additives then flow through the product chamber where they are cooled by a refrigerant flowing in the inner and outer cooling chambers. The mixed and cooled blood plasma and additives then flow from an outlet in the product chamber. A method is disclosed of continuously supplying a flow of blood plasma and desired additives in predetermined proportions and mixing and cooling the continuous flow of the combined blood plasma and additives.

15 Claims, 4 Drawing Figures

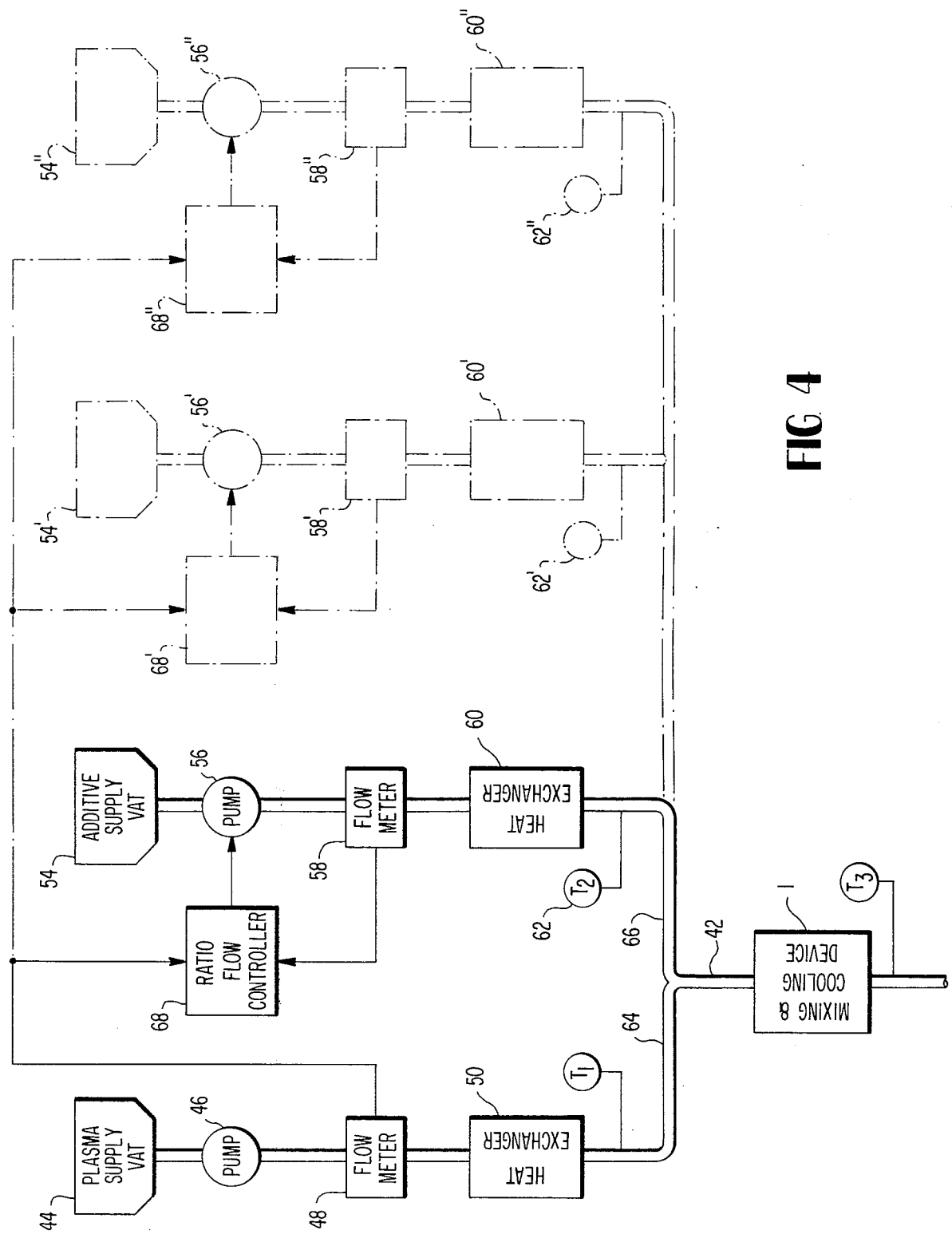

METHOD AND APPARATUS FOR CONTINUOUS MIXING OF BLOOD PLASMA AND ADDITIVES

FIELD OF THE INVENTION

The present invention relates to mixing, and more particularly, to a method and apparatus for continuous mixing of blood plasma with additives and for removing the heat of solution. All of this is carried out in continuous manner in a completely enclosed system.

BACKGROUND OF THE INVENTION

Present methods and apparatus for the mixing of blood plasma and additives in a process of fractionation have several important shortcomings. In the methods and apparatus of the art existing prior to the present invention, the plasma or supernatant is cooled in large jacketed vats. The amounts vary from one fractionator to another and several thousand liters can be involved at one time. Additions are slowly metered and mixing is achieved by stirring.

This process can taken several hours. The heat of solution is removed by a refrigerant which is circulated through a jacket surrounding the vat. There are several problems associated with this method of mixing. At the beginning of the procedure, there is an imbalance in the mix with the high concentrations of the additives being in localized spots in the vat. This can cause denaturization of the proteins and possible precipitation of unwanted proteins. The high concentrations of alcohol will cause a heat problem and possible denaturization of the proteins. In addition, the mixing process takes an extensive period of time, as long as 6 hours, and the whole batch of plasma is subjected to long-term alcohol denaturization, pyrogens and other possible damage that can cause the loss of the entire batch. Further, large batches of proper additives must be pre-cooled in order to help control the heat of solution.

Each batch of supernatant must be stored in refrigerated vats while waiting for the next fraction to be run. The whole process of batch fractionization is slow and cumbersome, requires many refrigerated vessels and requires constant attention and adjustment and many man-hours. Still another problem associated with batch mixing and handling is that frothing and bubbles can cause denaturization of the proteins that should be avoided. The system of automatically blending and handling plasma as described herein completely eliminates frothing.

SUMMARY OF THE INVENTION

It is therefore an object of the present invention to eliminate the problems existing in the prior art.

It is a further object of the present invention to provide a method and apparatus for the continuous rather than batch fractionation of blood plasma.

It is still another object of the present invention to limit the susceptibility of the plasma to long-term alcohol denaturization, pryogens and other possible damages which can occur during batch fractionization.

It is yet another object of the present invention to decrease the heat of the solution resulting from the present batch fractionation methods and to eliminate the problem of frothing experienced in batch fractionation methods.

These and other objects are accomplished in the present invention by providing a method and apparatus for the mixing and cooling of a continuous flow of blood plasma and desired additives, such as alcohol. The apparatus comprises an elongated cylindrical product chamber with inner and outer coolant chambers disposed internally and externally of the product chamber. The product chamber Plasma an impeller. Plasma and desired additives are introduced into the product chamber in the vicinity of the impeller which mixes the plasma and additives and forces the mixed blood plasma and additives through the remainder of the product chamber where it is cooled by a refrigerant flowing in the inner and outer cooling chambers. The mixed and cooled blood plasma and additives then flow out of the outlet in the product chamber.

The entire apparatus also includes means for continuously supplying the blood plasma to the mixing and cooling device and also preferably means for supplying desired additives, metered in desired amounts, dependent upon the flow of the plasma to the mixing and cooling device, and for precooling the plasma and additives prior to entry into the mixing and cooling device.

By using the apparatus of the present invention, a method of continuously mixing and cooling plasma and desired additives in a continuous flow in a completely enclosed system completely avoids the shortcomings of the present fractionators in use.

BRIEF DESCRIPTION OF THE DRAWING

The present invention can be more fully understood by reference to the detailed description of an embodiment of the invention as shown in the drawing wherein:

FIG. 4 shows a schematic view of an embodiment of the entire apparatus of the present invention used for carrying out the process of the present invention.

DETAILED DESCRIPTION

Figure 1:
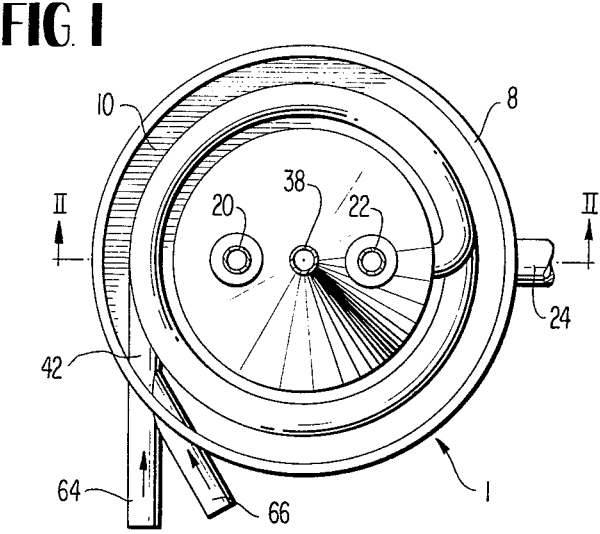
FIG. 1 shows a top plan view of the mixing apparatus of an embodiment of the present invention looking down in plane I—I of FIG. 2.

Referring to FIG. 1 which shows a top plan view of a mixing and cooling apparatus 1 of the present invention, there is shown an outer wall 8 of a cylindrical outer coolant chamber 10 with an inner coolant chamber refrigerant inlet 20 and outlet 22, and a product outlet 38 extending longitudinally upwards through an upper surface 11 of the outer coolant chamber 10. Also shown is a base 40 to which the entire apparatus is mounted. A product inlet 42, which contains a pair of branches 64 and 66 for plasma supply and additive supply, is shown to enter the apparatus through the outer wall 8 of the outer cooling chamber 10. An outer cooling chamber refrigerant outlet 24 extends radially outward from the upper end of the cylindrical outer wall 8 of the outer coolant chamber 10.

Figure 2:
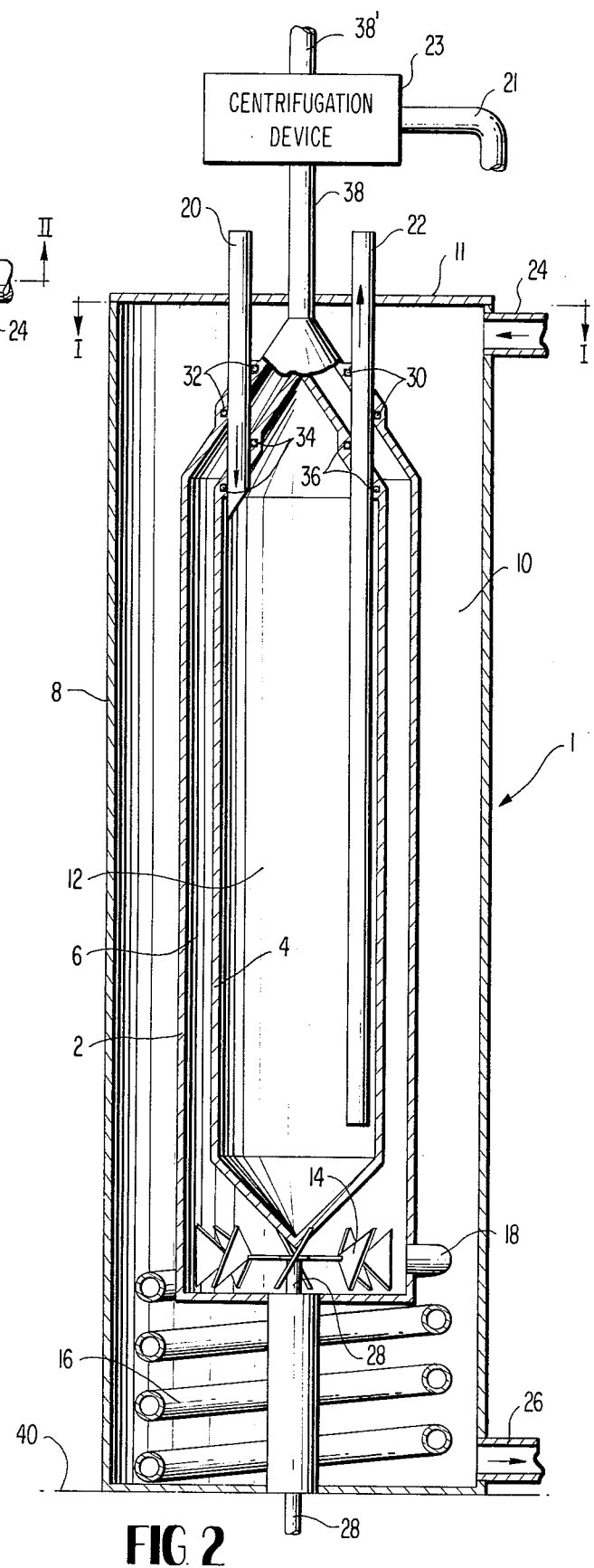
FIG. 2 shows a side elevational cutaway view along line II—II in FIG. 1.

Referring to FIG. 2, wherein like numerals indicate the same elements as in FIG. 1, a side elevational cutaway view of the mixing and cooling apparatus of FIG. 1 shows that the outer coolant chamber 10 is annular as defined by an inner wall. An inner coolant chamber 12 consists of an elongated cylindrical or tubular body 4 having closed substantially conical upper and lower ends.

A product chamber 6 of annular configuration is formed between the inner coolant chamber wall 4 and the inner wall 2 of the outer coolant chamber 10. The product chamber 6 narrows at the upper end thereof such that the wall 2 runs substantially parallel to the conical portion of the inner coolant chamber 12 and terminates in a product outlet 38. As shown schematically in FIG. 2, the product outlet 38 is connected to a centrifugation device which causes the desired fractionization precipitate to be separated from the plasma and additive mixture which then continues to flow out of centrifugation device outlet 38'. The desired precipitate is collected and transported through precipitate outlet 21 to storage.

The lower end of the product chamber 6 contains an impeller 14 mounted on an impeller shaft 28. A product cooling coil 16 extends from the inlet 42 and passes through the outer coolant chamber 10 to discharge a mixture of plasma and additives into the product chamber 6 in the vicinity of the impeller 14. The product inlet 18 is constructed to deliver the product into the product chamber 6 transversely to the longitudinal axis of the product chamber 6 and substantially tangential to the product chamber outer wall at the point of entry of the product.

The inner coolant chamber 12 is cooled by a refrigerant which is delivered to the inner coolant chamber through the inner coolant chamber refrigerant inlet 20. The refrigerant inlet 20 passes through the product chamber 6 and therefore, O-ring seals 32, 34 are used to prevent the product in the product chamber from contacting the refrigerant in the inner and outer coolant chambers 10, 12. The inner coolant chamber refrigerant outlet 22 consists of an elongated pipe which extends into the inner coolant chamber to substantially the lower extremity thereof. As with the refrigerant inlet 20, the refrigerant outlet 22 is provided with O-ring seals 30, 36. The outer coolant chamber 10 is supplied with refrigerant by the refrigerant inlet 24 and the refrigerant exits through an outlet 26.

In operation, the material to be fractionated and the proper additives are introduced into the mixing and cooling coil through the separate connections 64 and 66 forming the "Y" shown in FIG. 1. The material may be whole plasma or supernatant from a preceeding fractionation stage. Additives may be water, alcohol, buffers, or any combination thereof that will cause the desired selective precipitation of proteins.

The mixing and cooling device 1 is operated in the upright position, i.e. with the product outlet 38 is above the product inlet 42. This is due to the fact that the mixing and cooling device 1 depends to a certain extent on gravity to assist in the mixing process and also the fact that having the product inlet 42 below the product outlet 38 assures that the mixing and cooling device 1 is always full of liquid product. No air, liquid or solids can then become entrapped in the mixing and cooling device 1. This facilitates start-up since no means are required to insure the system is purged of air on start-up.

As this mixture passes through the cooling coil 16, heat of solution is partially removed. The cooling coil 16 is connected to the product chamber 6 at a height equal to approximately the axial center line of the impeller blade 14.

It will be noted that the cooling coil 16 could be eliminated from the mixing and cooling device 1 without significantly modifying the present invention. The mixing and cooling device 1, in that event would be less efficient; however, since the heat of solution created by joining the flow of the plasma and additives in the product inlet 42 is not instantaneous, and part of this heat of solution is removed in the cooling coil 16 prior to the product entering the product chamber 6 where final mixing and cooling occurs. The impeller 14 rotates against the flow of the material entering the product chamber 6 and the blades of the impeller 14 may be so constructed as to force the entering material down towards the lower extremity of the product chamber. Also, the direction of rotation of impeller 14 is not essential, however, it has been found that rotation against the flow of the entering product provides better mixing.

It has been found that an eight-blade impeller 14 rotating at a speed of 28 rpm will give a gentle agitation without causing frothing of the plasma which can be detrimental to the proteins. Of course, the impeller 14 could have blades constructed so as to force the entering material upwardly through the chamber 6 and toward the product outlet 38.

Coolant flow is directed to the inner and outer coolant chambers through the refrigerant inlets and outlets, respectively, 20, 24 and 22, 26. Of course, coolant may be introduced into either the inlet or the outlet for either of the coolant chambers; however, it is preferred to have the coolant flow in an opposite direction to the flow in the product chamber 6. This gives a better heat exchange characteristic of the heat exchanger portion of the mixing and cooling device 1.

Figure 3:
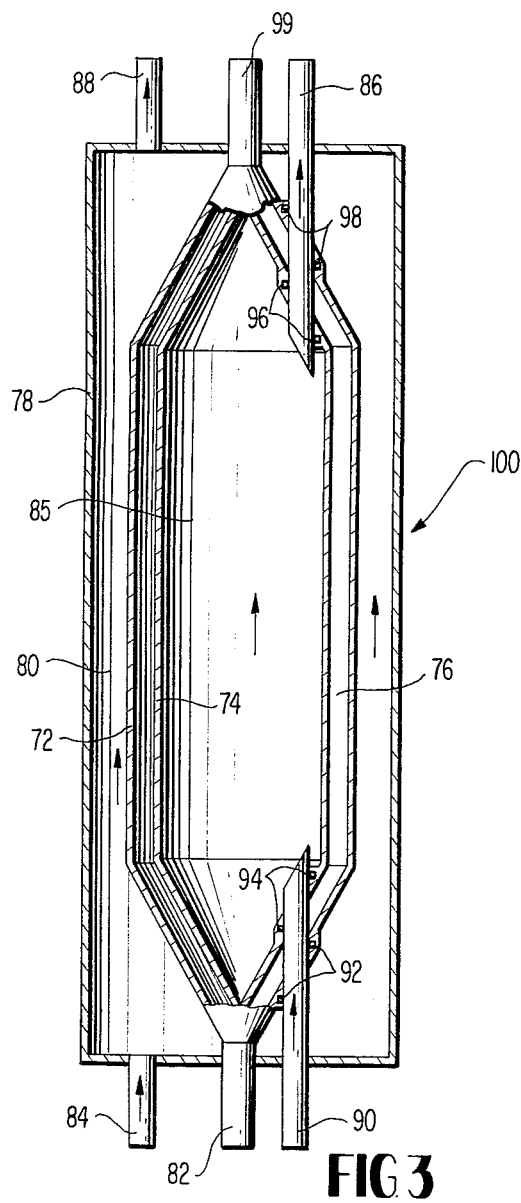
FIG. 3 shows a side elevational cutaway view of a heat exchanger cooling apparatus of the present invention.

An embodiment of a heat exchanger cooling device 100 of the present invention is shown in FIG. 3. The product chamber 76 of the heat exchanger cooling device 100 is formed between the inner coolant chamber 85 and the outer coolant chamber 80. The inner coolant chamber 85 has an outer wall 74 and the outer coolant chamber 80 has an inner wall 72, with the product chamber 76 being deviced therebetween. Plasma or additive are inserted into the heat exchanger cooling device 100 through an inlet 82 and extracted therefrom through an outlet 99. The outer coolant chamber 80 has an outer wall 78. As in the mixing and cooling device 1 there is a need to protect the plasma or additive in the product chamber 76 from the refrigerant in the inner and outer coolant chambers 85, 80. O-ring seals 92, 94 and 96, 98 are therefore provided for respectively the inner coolant chamber refrigerant inlet 90 and outlet 86. Plasma or additives are supplied from respective sources into a line which forms the inlet 82. Refrigerant is supplied to the inner and outer coolant chambers 85, 80 by, respectively, the refrigerant inlets 90, 84 and the refrigerant outlets 86, 88. In this embodiment the refrigerant is shown to flow in the same direction as the product flows through the heat exchanger portion of the cooling device 100, although refrigerant could flow through the heat exchanger cooling device 100 in a direction counter to the flow of the plasma or additive if desired.

In either the mixing and cooling device 1 or the heat exchanger cooling device 100 the flow rates of the plasma and additives, the transition time of the plasma and additives through the mixing and cooling device 1 and the heat exchanger cooling device 100 and the temperatures used within the mixing and cooling device 1 and the heat exchanger cooling device 100 depend upon several variables. The flow handling capabilities of the apparatus depend on chamber and pipe sizes and the amount of pressure build-up desired to be allowed in the mixing and cooling chamber and the heat exchanger cooling device. The transit time in the product chambers 6, 76 depends on the volume of the product chamber 6, 76 and the flow rate at which the plasma-additive mix is being delivered to the mixing and cooling device 1 and the plasma or additive are being delivered to the heat exchanger cooling device 100. The temperatures used in the device depend upon the alcohol content of the mixture. For example, starting plasma without any alcohol additives must be kept about freezing. With approximately 40% alcohol, however, the mix can be taken to −20°C. or lower without freezing.

FIG. 4 shows an entire system of the present invention. The system is for the continuous mixing and cooling of a constant flow of plasma and additives in a completely enclosed system. Plasma is supplied from the plasma supply vat 44 to the system by the plasma supply pump 46 through the plasma supply flow meter 48 and the plasma supply heat exchanger 50. The outlet of the plasma supply heat exchanger flows into the plasma supply line 64.

Additives such as buffers, alcohol, or water are supplied from the additive supply vat 54 to the system through the additive supply pump 56 through the additive supply flow meter 58. The additives are also pumped through the additive supply heat exchanger 60 which has an additive supply heat exchanger outlet temperature monitor 62. Both the plasma supply heat exchanger 50 and the additive supply heat exchanger 60 may be constructed similarly to the heat exchanger cooling device 100 of FIG. 3.

With the use of the continuous flow system of the present invention containing plasma heat exchanger 50 and one or more additive heat exchangers 60, the need in the existing art to maintain the plasma supply vat 44 or the additive supply vat 54 (or plurality of additive supply vats 59 as desired) at a reduced temperature below room temperature is eliminated. The continuous flow method, in addition, eliminates the need in the existing art of fractionization process to keep the room temperature reduced while the plasma and additives are mixing in the open vat normally used in the existing art.

The outlet of the additive supply heat exchanger 60 flows into the additive supply line 66. The plasma supply line 64 and the additive supply line 66 are joined together to form a product inlet 42 of the mixing and cooling cell 1 of the present invention. Also shown in FIG. 4 is the flow ratio controller 68. The flow ratio controller has two inputs from the plasma flow meter 48 and from the additive flow meter 58. Dependent upon a desired ratio between the plasma flow and the additive flow, the flow ratio controller will compare the plasma flow and the additive flow to the desired proportions and alter the additive flow as necessary by changing the speed of the additive flow pump 56.

The plasma heat exchanger outlet temperature monitor 52, the additive heat exchanger outlet temperature monitor 62 and the mixing and cooling device outlet temperature monitor 70 can be used to manually or automatically control the refrigerant flow respectively to the plasma supply heat exchanger 50, the additive supply heat exchanger 60 and the product mixing and cooling device 1 in order to maintain desired temperatures in the respective parts of the system.

Of course, the system shown in FIG. 4 can be modified to include a plurality of additive supply vats 54 with associated pumps 56, meters 58, heat exchangers 60 and temperature monitors 62. In this event, a plurality of flow ratio controllers 68 would be provided to control the ratio of flow of a particular additive to the flow of plasma.

This is shown in phantom in FIG. 4 where the additional additive supply vats 54, pumps 56, flow meters 58, heat exchanger cooling devices 60, additive temperature gauges 62 and ratio flow controllers 68 are indicated by primes.

The process of the present invention using the apparatus disclosed herein automatically blends the plasma and additives in a continuous flowthrough basis. The pre-set ratios are monitored and maintained by a closed loop control system including the ratio flow controller 68. The process eliminates the necessity to pre-cool the plasma and additives in the storage vats 44, 54 to control the heat of solution. Additives can be introduced into the system used in the process at ambient temperatures from the additive storage vat 54. This eliminates the need for additional refrigerated tanks and refrigerant required in devices and process of the existing art. The entire process can be carried out with room temperature external to all of the components of the system in contrast to the requirement in the existing art that the process of fractionization be carried out in a room having reduced temperature.

It can be readily seen from the above description that the apparatus and system of the present invention provides for a system and method of continuous flow mixing and cooling of plasma and desired additives which avoids the shortcomings of the batch type fractionation systems of the prior art.

It will be obvious to those skilled in the art that various changes may be made without departing from the scope of the invention and the invention is not to be considered limited to what is shown in the drawings and described in the specification.

What is claimed is:

1. An apparatus for the continuous mixing of blood plasma with additives such as alcohol and for cooling said mixture comprising;
    a first product chamber having first and second ends;
    a first inner coolant chamber coaxially disposed internal to said first product chamber;
    a first outer coolant chamber coaxially disposed external to said first product chamber;
    input means for introducing plasma and at least one additive such as alcohol into said first product chamber at said first end thereof;
    means for mixing the plasma and the additive, said means being located in said first product chamber near the first end thereof;
    first inlet means and first outlet means for creating a flow of refrigerant through said first inner coolant chamber;
    second inlet means and second outlet means for creating a flow of refrigerant through said first outer coolant chamber; and
    a product outlet connected to said first product chamber at said second end thereof.

2. The apparatus according to claim 1, wherein said input means includes;
    a plasma supply pipe;
    an additive supply pipe;

a product cooling coil connected to said plasma supply pipe and said additive supply pipe, said product cooling coil being contained within said outer coolant chamber and having a discharge opening into said product chamber at said one end thereof.

3. The apparatus according to claim 2 wherein said discharge end is attached to said first product chamber such that the flow of the plasma and additive is essentially tangential to the inner surface of said first product chamber and essentially transverse to the longitudinal axis of said first product chamber.

4. The apparatus according to claim 2 further including:
a plasma supply system connected to said plasma supply pipe;
an additive supply system connected to said additive supply pipe;
said plasma supply system including:
a plasma supply vat;
a plasma supply pump the inlet of which is connected to said plasma supply vat;
a plasma flow meter having an inlet connected to the outlet of said plasma supply pump, and an outlet;
a plasma heat exchanger having an inlet connect to said outlet of said plasma flow meter, and an outlet connected to said plasma supply pipe;
said additive supply system including:
an additive supply vat;
an additive supply pump the inlet of which is connected to said additive supply vat;
an additive flow meter having an inlet connected to the outlet of said additive supply pump, and an outlet;
an additive heat exchanger having an inlet connected to said outlet of said additive flow meter, and an outlet connected to said additive supply pipe; and
means, connected to said plasma flow meter and said additive flow meter, for regulating the flow of the additive dependent upon the flow of the plasma from said plasma supply pump.

5. The apparatus according to claim 4 wherein said plasma heat exchanger and said additive heat exchanger are each comprised of
a second product chamber having first and second ends
a second inner coolant chamber axially disposed internal to said second product chamber;
a second outer coolant chamber axially disposed external to said second product chamber;
inlet means for introducing a fluid into said second product chamber at said first end thereof;
output means for extracting said fluid from said second product chamber at said second end thereof;
third inlet means and third outlet means for creating a flow of refrigerant through said second inner coolant chamber; and
fourth inlet means and fourth outlet means for creating a flow of refrigerant through said second outer coolant chamber.

6. The apparatus of claim 1 wherein said mixing means comprises an impeller rotatably mounted in said first product chamber at said first end thereof and driving means for rotating said impeller.

7. The apparatus according to claim 6 wherein said impeller has a plurality of blades and rotates in a direction opposite to the direction of the flow of plasma and additive into said first product chamber.

8. The apparatus according to claim 6 wherein said impeller has a plurality of blades and rotates in the same direction as the direction of the flow of plasma and additive into said product chamber.

9. The apparatus according to claim 1 further including at least one heat exchanger cooling device comprising:
a second product chamber having first and second ends;
a second inner coolant chamber axially disposed internal to said second product chamber;
a second outer coolant chamber axially disposed external to said second product chamber;
inlet means for introducing a fluid into said second product chamber at said first end thereof;
output means for extracting said fluid from said second product chamber at said second end thereof;
third inlet means and third outlet means for creating a flow of refrigerant through said second inner coolant chamber; and
fourth inlet means and fourth outlet means for creating a flow of refrigerant through said second outer coolant chamber.

10. The apparatus to claim 9 wherein said input means is spaced below said product outlet, and
said inelt means is spaced below said outlet means.

11. The apparatus according to claim 9 wherein said at least one heat exchanger cooling device includes first and second heat exchanger cooling devices; and
said fluid flowing through said first heat exchanger cooling device is plasma, and said fluid flowing through said second heat exchanger cooling device is an additive.

12. The apparatus according to claim 9 wherein said at least one heat exchanger cooling device includes a first heat exchanger cooling device and a plurality of second heat exchanger cooling devices; and
said fluid flowing through said first heat exchanger cooling device is plasma, and said fluid flowing through each of said plurality of second heat exchanger devices is selected from a plurality of desired additives.

13. The apparatus according to claim 1 wherein said input means is spaced below said product outlet.

14. A method of mixing and cooling plasma and at least one additive including the steps of:
continuously supplying a flow of plasma to the bottom of a vertically disposed mixing and cooling heat exchanger having a central coolant chamber and an outer chamber, said coolant chambers being separated by an annular flow passageway;
continuously supplying a flow of at least one desired non-gaseous additive, in a proportion dependent upon the flow of plasma, to the bottom of said mixing and cooling heat exchanger;
continuously mixing said plasma and said non-gaseous additive;
continuously feeding the mixture of plasma and additive upwardly through said annular flow passageway between said coolant chambers to cool said mixture; and
continuously withdrawing a product, consisting of mixed and cooled plasma and said at least one desired additive, from said mixing and cooling heat exchanger.

15. A device for use in blood plasma fractionation for continuously cooling blood plasma without entrapment of air, comprising:

an annular product passageway having a top end and a bottom end;

an inner coolant chamber coaxially disposed internal to said annular product passageway;

an outer coolant chamber coaxially disposed external to said annular product passageway;

inlet means at said bottom end of said annular passageway for introducing blood plasma into said annular passageway;

outlet means at the upper end of said annular passage for removing said plasma from said annular passageway;

first refrigerant inlet means and first refrigerant outlet means for passing refrigerant into and out of said first coolant chamber; and second refrigerant inlet means and second refrigerant outlet means for passing refrigerant into and out of said second outer coolant chamber.

* * * * *